(12) United States Patent
Netzel et al.

(10) Patent No.: US 11,076,910 B2
(45) Date of Patent: Aug. 3, 2021

(54) JAW MEMBERS FOR SURGICAL INSTRUMENTS AND SURGICAL INSTRUMENTS INCORPORATING THE SAME

(71) Applicant: COVIDIEN LP, Mansfield, MA (US)

(72) Inventors: Kenneth E. Netzel, Loveland, CO (US); Jason L. Craig, Loveland, CO (US)

(73) Assignee: Covidien LP, Mansfield, MA (US)

( * ) Notice: Subject to any disclaimer, the term of this patent is extended or adjusted under 35 U.S.C. 154(b) by 227 days.

(21) Appl. No.: 15/876,691

(22) Filed: Jan. 22, 2018

(65) Prior Publication Data

US 2019/0223939 A1 Jul. 25, 2019

(51) Int. Cl.
*A61B 18/14* (2006.01)
*A61B 17/295* (2006.01)
(Continued)

(52) U.S. Cl.
CPC ........ *A61B 18/1445* (2013.01); *A61B 17/282* (2013.01); *A61B 17/29* (2013.01); *A61B 17/295* (2013.01); *A61B 17/320092* (2013.01); *A61B 2017/2926* (2013.01); *A61B 2017/2939* (2013.01); *A61B 2017/2944* (2013.01);
(Continued)

(58) Field of Classification Search
CPC ................ A61B 18/1445; A61B 17/29; A61B 17/320092; A61B 17/295; A61B 17/282; A61B 2017/2926; A61B 2017/320094; A61B 2017/2939; A61B 2018/1455;
(Continued)

(56) References Cited

U.S. PATENT DOCUMENTS 2,397,823 A * 4/1946 Walter ............... A61B 17/2812
606/207
3,404,683 A * 10/1968 Eizenberg .......... A61B 17/2812
606/207
(Continued)

FOREIGN PATENT DOCUMENTS

EP 1518505 A1 3/2005
EP 2361048 A2 8/2011
(Continued)

OTHER PUBLICATIONS

Extended European Search Report issued in corresponding European Application No. 19152735.7 dated Apr. 17, 2019, 9 pages.

*Primary Examiner* — Julian W Woo
(74) *Attorney, Agent, or Firm* — Carter, DeLuca & Farrell LLP (57) ABSTRACT

A jaw member for a surgical instrument includes a structural body including a proximal flange portion and an elongated distal portion extending distally from the proximal flange portion. The elongated distal portion includes a base and first and second sidewalls extending from either side of the base along at least a portion of a length of the elongated distal portion. A jaw liner is engaged with the base of the elongated distal portion and defines a tissue-contacting surface. The first and second sidewalls extend beyond the tissue-contacting surface of the jaw liner and are configured to facilitate gripping tissue between the structural body and an opposed structure. A surgical instrument including such a jaw member is also provided.

16 Claims, 5 Drawing Sheets

(51) Int. Cl.
*A61B 17/28* (2006.01)
*A61B 17/29* (2006.01)
*A61B 17/32* (2006.01)

(52) U.S. Cl.
CPC .............. *A61B 2017/2945* (2013.01); *A61B 2017/320094* (2017.08); *A61B 2018/1455* (2013.01); *A61B 2018/1457* (2013.01)

(58) Field of Classification Search
CPC .... A61B 2018/1457; A61B 2017/2945; A61B 2017/2944
See application file for complete search history.

(56) References Cited

U.S. PATENT DOCUMENTS

| | | | |
|---|---|---|---|
| 3,469,211 A | 9/1969 | Shoh | |
| 3,503,396 A * | 3/1970 | Pierie | A61B 17/282 606/207 |
| 4,277,710 A | 7/1981 | Harwood et al. | |
| 4,587,958 A | 5/1986 | Noguchi et al. | |
| 4,827,911 A | 5/1989 | Broadwin et al. | |
| 4,922,902 A | 5/1990 | Wuchinich et al. | |
| 4,965,532 A | 10/1990 | Sakurai | |
| 4,973,876 A | 11/1990 | Roberts | |
| 5,014,407 A | 5/1991 | Boughten et al. | |
| 5,180,363 A | 1/1993 | Idemoto et al. | |
| 5,216,338 A | 6/1993 | Wilson | |
| 5,304,203 A | 4/1994 | El-Mallawany et al. | |
| 5,330,502 A | 7/1994 | Hassler et al. | |
| 5,421,829 A | 6/1995 | Olichney et al. | |
| 5,456,684 A | 10/1995 | Schmidt et al. | |
| 5,532,539 A | 7/1996 | Hielscher | |
| 5,562,682 A | 10/1996 | Oberlin et al. | |
| 5,634,466 A | 6/1997 | Gruner | |
| 5,637,947 A | 6/1997 | Kising et al. | |
| 5,649,957 A | 7/1997 | Levin | |
| 5,674,220 A * | 10/1997 | Fox | A61B 18/1442 606/205 |
| 5,700,952 A | 12/1997 | Andersen | |
| 5,702,408 A | 12/1997 | Wales et al. | |
| 5,704,534 A | 1/1998 | Huitema et al. | |
| 5,797,537 A | 8/1998 | Oberlin et al. | |
| 5,816,476 A | 10/1998 | Buice et al. | |
| 5,817,119 A | 10/1998 | Klieman et al. | |
| 5,819,738 A * | 10/1998 | Slater | A61B 10/06 600/564 |
| 5,873,873 A | 2/1999 | Smith et al. | |
| 5,897,523 A | 4/1999 | Wright et al. | |
| 6,063,098 A | 5/2000 | Houser et al. | |
| 6,068,647 A | 5/2000 | Witt et al. | |
| 6,099,550 A * | 8/2000 | Yoon | A61B 10/06 606/205 |
| 6,129,735 A | 10/2000 | Okada et al. | |
| 6,163,100 A | 12/2000 | Morizaki et al. | |
| 6,193,709 B1 | 2/2001 | Miyawaki et al. | |
| 6,241,139 B1 | 6/2001 | Milliman et al. | |
| 6,320,298 B1 | 11/2001 | Kawabe | |
| 6,454,782 B1 | 9/2002 | Schwemberger | |
| 6,480,796 B2 | 11/2002 | Wiener | |
| 6,569,109 B2 | 5/2003 | Sakurai et al. | |
| 6,588,277 B2 | 7/2003 | Giordano et al. | |
| 6,626,926 B2 | 9/2003 | Friedman et al. | |
| 6,652,547 B2 | 11/2003 | Rabiner et al. | |
| 6,663,641 B1 | 12/2003 | Kovac et al. | |
| 6,666,854 B1 | 12/2003 | Lange | |
| 6,678,621 B2 | 1/2004 | Wiener et al. | |
| 6,679,899 B2 | 1/2004 | Wiener et al. | |
| 6,752,815 B2 | 6/2004 | Beaupre | |
| 6,761,690 B2 | 7/2004 | Sakurai et al. | |
| 6,770,072 B1 * | 8/2004 | Truckai | A61B 18/1445 606/52 |
| 6,887,252 B1 | 5/2005 | Okada et al. | |
| 6,898,536 B2 | 5/2005 | Wiener et al. | |
| 6,958,070 B2 * | 10/2005 | Witt | A61B 17/320092 606/169 |
| 6,984,919 B2 | 1/2006 | Iino et al. | |
| 7,179,271 B2 | 2/2007 | Friedman et al. | |
| 7,247,141 B2 | 7/2007 | Makin et al. | |
| 7,264,618 B2 | 9/2007 | Murakami et al. | |
| 7,270,646 B2 | 9/2007 | Sakurai et al. | |
| 7,273,483 B2 | 9/2007 | Wiener et al. | |
| 7,475,801 B2 | 1/2009 | Johansen et al. | |
| 7,481,824 B2 | 1/2009 | Boudreaux et al. | |
| 7,482,888 B1 | 1/2009 | Kleveland | |
| 7,503,895 B2 | 3/2009 | Rabiner et al. | |
| 7,513,160 B2 | 4/2009 | Lynch et al. | |
| 7,514,844 B2 | 4/2009 | Unkrich | |
| 7,528,670 B2 | 5/2009 | Soh | |
| 7,544,200 B2 | 6/2009 | Houser | |
| 7,566,334 B2 | 7/2009 | Christian et al. | |
| 7,614,878 B2 | 11/2009 | Paschke et al. | |
| 7,749,222 B2 | 7/2010 | Lu et al. | |
| 8,002,782 B2 | 8/2011 | Witt et al. | |
| 8,057,467 B2 | 11/2011 | Faller et al. | |
| 8,292,888 B2 | 10/2012 | Whitman | |
| 8,361,071 B2 * | 1/2013 | Tetzlaff | A61B 18/1445 606/51 |
| 8,366,727 B2 | 2/2013 | Witt et al. | |
| 8,444,664 B2 | 5/2013 | Balanev et al. | |
| 8,469,982 B2 | 6/2013 | Witt et al. | |
| 8,469,993 B2 * | 6/2013 | Rothberg | A61B 10/06 600/564 |
| 8,518,067 B2 | 8/2013 | Masuda et al. | |
| 8,523,890 B2 | 9/2013 | Whitman | |
| 8,535,340 B2 | 9/2013 | Allen | |
| 8,579,897 B2 | 11/2013 | Vakharia et al. | |
| 8,672,959 B2 | 3/2014 | Witt et al. | |
| 8,715,306 B2 | 5/2014 | Faller et al. | |
| 8,773,001 B2 * | 7/2014 | Wiener | A61B 18/1445 310/323.01 |
| 9,044,261 B2 | 6/2015 | Houser | |
| 9,414,853 B2 | 8/2016 | Stulen et al. | |
| 9,439,670 B2 | 9/2016 | Witt et al. | |
| 9,649,152 B2 * | 5/2017 | Moua | A61B 18/1445 |
| 9,724,120 B2 | 8/2017 | Faller et al. | |
| 9,867,659 B2 * | 1/2018 | Brandt | B29C 70/78 |
| 9,943,357 B2 * | 4/2018 | Cunningham | A61B 18/1445 |
| 9,956,030 B2 * | 5/2018 | Allen, IV | A61B 18/1445 |
| 10,368,940 B2 * | 8/2019 | Mensch | A61B 18/1447 |
| 10,905,451 B2 * | 2/2021 | Kappel | A61B 18/1445 |
| 2002/0002380 A1 | 1/2002 | Bishop | |
| 2002/0111622 A1 | 8/2002 | Khandkar et al. | |
| 2003/0114874 A1 | 6/2003 | Craig et al. | |
| 2004/0097911 A1 | 5/2004 | Murakami et al. | |
| 2005/0027311 A1 | 2/2005 | Wiener et al. | |
| 2005/0070800 A1 | 3/2005 | Takahashi | |
| 2005/0143769 A1 | 6/2005 | White et al. | |
| 2005/0192610 A1 | 9/2005 | Houser et al. | |
| 2006/0100646 A1 | 5/2006 | Hart et al. | |
| 2006/0190031 A1 | 8/2006 | Wales et al. | |
| 2007/0179526 A1 | 8/2007 | Hart et al. | |
| 2007/0282332 A1 | 12/2007 | Witt et al. | |
| 2008/0188877 A1 | 8/2008 | Hickingbotham | |
| 2008/0234711 A1 | 9/2008 | Houser et al. | |
| 2008/0277447 A1 | 11/2008 | Smith et al. | |
| 2008/0294191 A1 | 11/2008 | Lee | |
| 2008/0308607 A1 | 12/2008 | Timm et al. | |
| 2009/0030311 A1 | 1/2009 | Stulen et al. | |
| 2009/0030439 A1 | 1/2009 | Stulen | |
| 2009/0036913 A1 | 2/2009 | Wiener et al. | |
| 2009/0036914 A1 | 2/2009 | Houser | |
| 2009/0065549 A1 | 3/2009 | Viola | |
| 2009/0069842 A1 | 3/2009 | Lee et al. | |
| 2009/0076534 A1 | 3/2009 | Shelton, IV et al. | |
| 2009/0118751 A1 | 5/2009 | Wiener et al. | |
| 2009/0131962 A2 | 5/2009 | Houser et al. | |
| 2009/0143797 A1 | 6/2009 | Smith et al. | |
| 2009/0143800 A1 | 6/2009 | Deville et al. | |
| 2009/0143806 A1 | 6/2009 | Witt et al. | |
| 2009/0182365 A1 | 7/2009 | Cuny | |
| 2009/0187185 A1 | 7/2009 | Lyons et al. | |
| 2009/0198272 A1 | 8/2009 | Kerver et al. | |

(56) References Cited

U.S. PATENT DOCUMENTS

| | | |
|---|---|---|
| 2009/0264909 A1 | 10/2009 | Beaupre |
| 2010/0030248 A1 | 2/2010 | Palmer et al. |
| 2010/0179545 A1 | 7/2010 | Twomey et al. |
| 2012/0296356 A1 | 11/2012 | Balanev et al. |
| 2012/0310229 A1 | 12/2012 | Gregg |
| 2013/0030328 A1 | 1/2013 | Dycus et al. |
| 2013/0085419 A1 | 4/2013 | Stoddard et al. |
| 2013/0121366 A1 | 5/2013 | Misuchenko et al. |
| 2013/0197511 A1 | 8/2013 | Balanev et al. |
| 2013/0325047 A1 | 12/2013 | Craig |
| 2014/0276735 A1 | 9/2014 | Boudreaux et al. |
| 2015/0297255 A1 | 10/2015 | Fan et al. |

FOREIGN PATENT DOCUMENTS

| | | |
|---|---|---|
| EP | 3207884 A1 | 8/2017 |
| EP | 3216410 A1 | 9/2017 |
| WO | 2011/008672 A2 | 1/2011 |
| WO | 2012/061645 A1 | 5/2012 |
| WO | 2015/137139 A1 | 9/2015 |

\* cited by examiner

JAW MEMBERS FOR SURGICAL INSTRUMENTS AND SURGICAL INSTRUMENTS INCORPORATING THE SAME

BACKGROUND

Technical Field

The present disclosure relates to surgical instruments and, more particularly, to jaw members of energy-based surgical instruments and energy-based surgical instruments incorporating the same.

Background of Related Art

Many energy-based surgical instruments employ an end effector including one or more jaw members configured to facilitate clamping, manipulating, and/or applying energy to tissue to treat tissue.

Ultrasonic surgical instruments, for example, utilize ultrasonic energy in the form of ultrasonic vibrations to coagulate, cauterize, fuse, seal, cut, desiccate, fulgurate, or otherwise treat tissue. The ultrasonic energy is typically produced by a generator and transducer and is transmitted along a waveguide to an end effector of the ultrasonic surgical instrument. The end effector may include a blade that receives the ultrasonic energy from the waveguide for application to tissue and a jaw member configured to clamp tissue between the blade and the jaw member to facilitate treatment thereof.

As vibrations induced in the blade and thermal energy generated by the blade may be transferred to the jaw member, jaw members have been developed that include a jaw liner engaged to a structural body of the jaw member. While inhibiting vibrations and thermal energy from being transferred to the structural body, there is a need to ensure tissue is securely clamped and maintained in position between the blade and jaw member during tissue treatment.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

Provided in accordance with aspects of the present disclosure is a jaw member for a surgical instrument including a structural body and a jaw liner. The structural body includes a proximal flange portion and an elongated distal portion extending distally from the proximal flange portion. The elongated distal portion includes a base and first and second sidewalls extending from either side of the base along at least a portion of a length of the elongated distal portion. The jaw liner is engaged with the base of the elongated distal portion and defines a tissue-contacting surface. The first and second sidewalls extend beyond the tissue-contacting surface of the jaw liner and are configured to facilitate gripping tissue between the structural body and an opposed structure.

In aspects, the sidewalls each define a plurality of gipping teeth.

In aspects, the plurality of gripping teeth have substantially similar heights or different heights.

In aspects, the plurality of gripping teeth are substantially equally spaced or differently spaced along the sidewalls.

In aspects, the gripping teeth only extend along a distal portion of the elongated distal portion of the structural body, only extend along a proximal portion of the elongated distal portion of the structural body, or extend along substantially the entire length of the elongated distal portion of the structural body.

A surgical instrument provided in accordance with aspects of the present disclosure includes an energy-delivering component and a jaw member positioned to oppose the energy-delivering component and movable relative thereto between an open position and a closed position for clamping tissue between the jaw member and the energy-delivering component. The jaw member may be configured similarly to any of the above aspects or as otherwise detailed herein.

In aspects, the energy-delivering component is an ultrasonic blade.

BRIEF DESCRIPTION OF THE DRAWINGS

The above and other aspects and features of the present disclosure will become more apparent in view of the following detailed description when taken in conjunction with the accompanying drawings, wherein.

DETAILED DESCRIPTION

Figure 1:
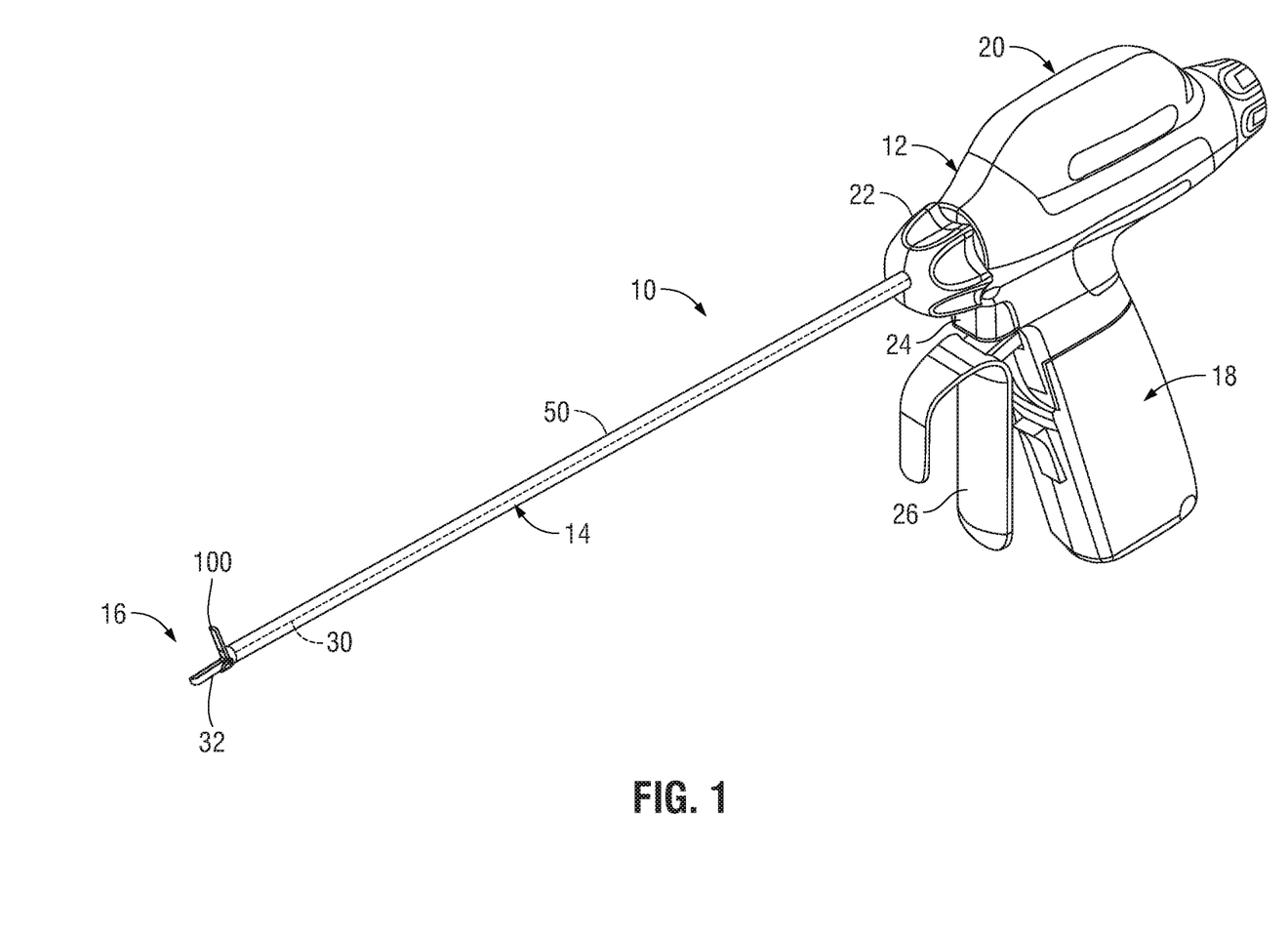
FIG. 1 is a perspective view of an ultrasonic surgical instrument including an end effector disposed in an open condition.

Jaw members and surgical instruments including such jaw members are provided in accordance with the present disclosure and detailed hereinbelow. Referring to FIG. 1, although the jaw members of the present disclosure are described for use with an ultrasonic surgical instrument 10, the jaw members of the present disclosure may alternatively be configured for use with any other suitable surgical instrument, including ultrasonic surgical instruments different from ultrasonic surgical instrument 10.

Ultrasonic surgical instrument 10 generally includes a handle assembly 12, an elongated body portion 14, and an end effector 16. Handle assembly 12 supports a power supply, e.g., a battery assembly 18, and an ultrasonic transducer and generator assembly ("TAG") 20, although ultrasonic surgical instrument 10 may alternatively be configured as a tethered instrument wherein the power supply and generator are remote components coupled to handle assembly 12 via one or more surgical cables (not shown). Handle assembly 12 includes a rotation wheel 22, an activation button 24, and a clamp trigger 26. Battery assembly 18 and TAG 20 are each releasably coupled to handle assembly 12 and are removable therefrom to facilitate disposal of any disposable components, e.g., handle assembly 12, elongated body portion 14, and/or end effector 16, and reprocessing of any reusable components, e.g., battery assembly 18 and TAG 20.

Figure 2A:
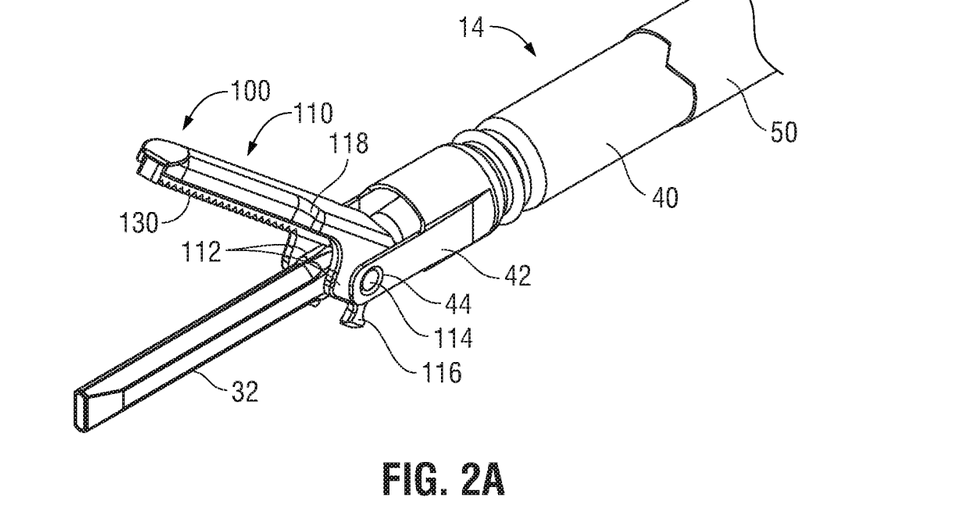
FIG. 2A is an enlarged, perspective view of a distal end portion of the ultrasonic surgical instrument of FIG. 1A, wherein the end effector is disposed in the open condition and wherein a distal portion of the outer sleeve is removed to illustrate the components hidden thereby.
Figure 2B:
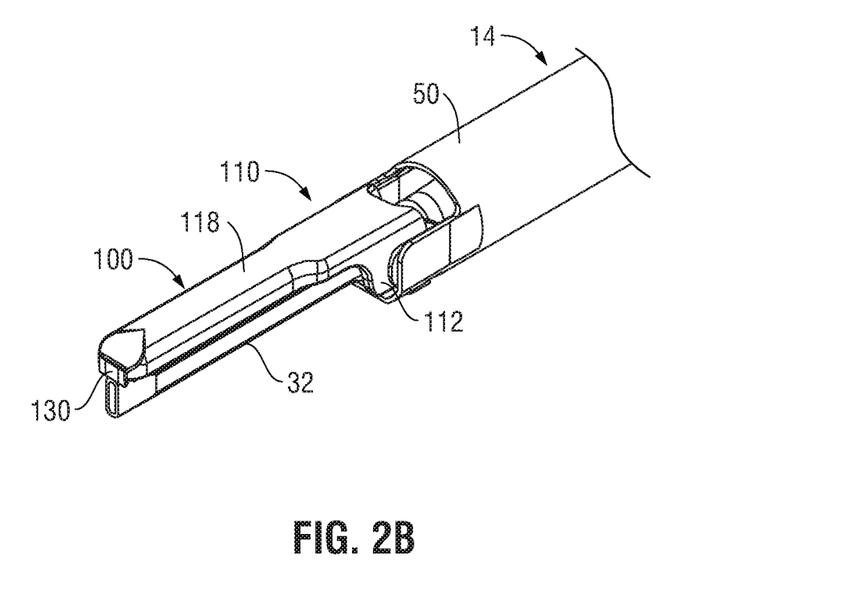
FIG. 2B is an enlarged, perspective view of the distal end portion of the ultrasonic surgical instrument of FIG. 1A, wherein the end effector is disposed in a clamping condition.

With additional reference to FIGS. 2A and 2B, elongated body portion 14 includes a waveguide 30 which extends from handle assembly 12 to end effector 16. A blade 32 of end effector 16 extends distally from waveguide 30. A proximal end portion of waveguide 30 is configured to engage the ultrasonic transducer of TAG 20 to enable the transmission of ultrasonic energy along waveguide 30 from the ultrasonic transducer of TAG 20 to blade 32.

Elongated body portion 14 further includes an inner tube 40 disposed about waveguide 30 and extending between handle assembly 12 and end effector 16. Inner tube 40, more specifically, includes a proximal end portion that extends into handle assembly 12. Inner tube 40 further includes a distal end portion including a pair of spaced-apart support arms 42 (only one of which is illustrated in FIG. 2A), each defining a transverse aperture 44 therethrough. Apertures 44 are configured to pivotably receive pivot bosses 114 of proximal flanges 112 of structural body 110 of jaw member 100 of end effector 16 to pivotably engage jaw member 100 to inner tube 40 at the distal end portion thereof.

An outer tube 50 is slidably disposed about inner tube 40 and similarly extends between handle assembly 12 and end effector 16. Outer tube 50, more specifically, includes a proximal end portion that extends into handle assembly 12 and operably couples to clamp trigger 26 by way of a drive assembly (not shown), and a distal end portion defining a cut-out (not shown) that operably receives legs 116 of proximal flanges 112 of structural body 110 of jaw member 100. As a result of this configuration, clamp trigger 26 may be manipulated between an un-actuated position and an actuated position to translate outer tube 50 between an advanced position and a retracted position, thereby pivoting jaw member 100 between an open position (FIGS. 1 and 2A), wherein jaw member 100 is spaced-apart from blade 32, and a closed position (FIG. 2B), wherein jaw member 100 is approximated relative to blade 32. Alternatively, the arrangement of inner and outer tubes 40, 50, respectively, may be reversed.

Rotation wheel 22 is operably coupled to waveguide 30, inner tube 40, and outer tube 50 such that rotation of rotation wheel 22 relative to handle assembly 12 similarly rotates waveguide 30, inner tube 40, and outer tube 50 relative to handle assembly 12, thereby also rotating blade 32 and jaw member 100 relative to handle assembly 12 in a similar manner. Activation button 24 is configured to selectively activate battery assembly 18 and TAG 20 to produce ultrasonic energy that is transmitted along waveguide 30 to blade 32 of end effector 16.

As detailed above, jaw member 100 includes a structural body 110 including a pair of proximal flanges 112 which enable pivotable coupling of jaw member 100 with inner tube 40 and operable coupling of jaw member 100 with outer tube 50. Structural body 110 of jaw member 100 further includes an elongated distal portion 118 extending distally from the pair of proximal flanges 112. A jaw liner 130 is engaged with elongated distal portion 118 of structural body 110 and is positioned to oppose blade 32 such that blade 32 is inhibited from contacting structural body 110 of jaw member 100. As a result, the transfer of ultrasonic vibrations and/or thermal energy from blade 32 to structural body 110 during use is reduced. Jaw liner 130 may be formed from a compliant material, e.g., PTFE, or maybe otherwise formed.

With general reference to FIGS. 1-2B, in use, ultrasonic instrument 10 is advanced into a surgical site and manipulated such that end effector 16 is positioned with tissue to be treated disposed between jaw member 100 and blade 32 with jaw member 100 disposed in the open position (FIGS. 1 and 2A). Thereafter, clamp trigger 26 is squeezed towards battery assembly 18 from the un-actuated position to the actuated position to translate outer tube 50 about inner tube 40 and relative to end effector 16, thereby pivoting jaw member 100 relative to blade 32 from the open position to the closed position to clamp tissue between jaw member 100 and blade 32 and, more specifically, between jaw liner 130 of jaw member 100 and blade 32. Blade 32 may then be activated, e.g., via depression of activation button 24, to supply ultrasonic energy from TAG 20, along waveguide 30, to blade 32. The ultrasonic energy provided at blade 32 is used to treat, e.g., coagulate, cauterize, fuse, seal, cut, desiccate, fulgurate, etc., tissue clamped between jaw member 100 and blade 32.

With reference to FIGS. 3A-5C, various different jaw members 200, 300, 400 configured for use ultrasonic instrument 10 are described. Each jaw member 200, 300, 400 is similar to jaw member 100, and may include any of the features thereof, except as specifically contradicted below.

Figure 3A:
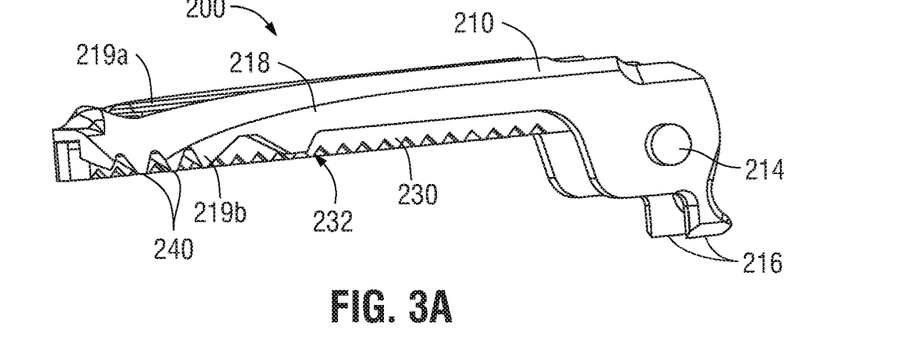
FIGS. 3A-3C are various views of a jaw member provided in accordance with the present disclosure and configured for use with the end effector of the ultrasonic surgical instrument of FIG. 1.
Figure 3B:
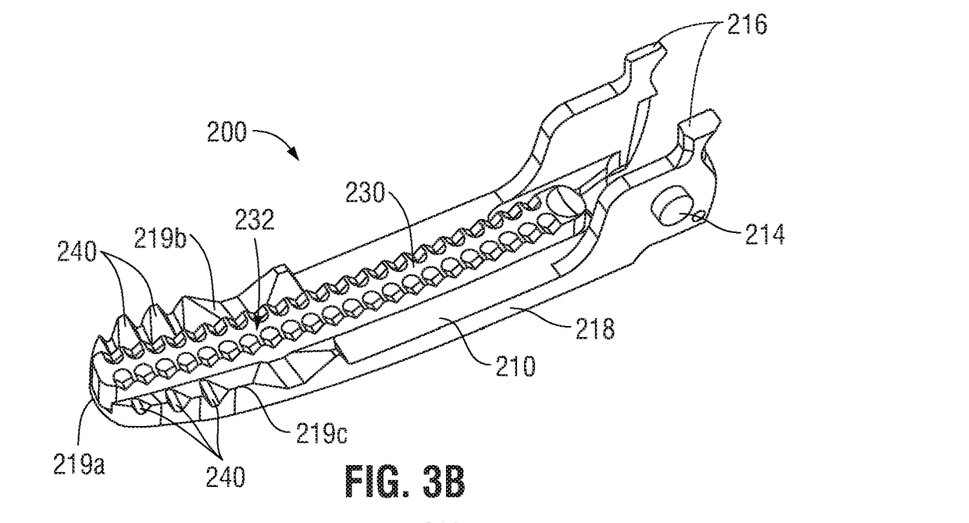
Figure 3C:
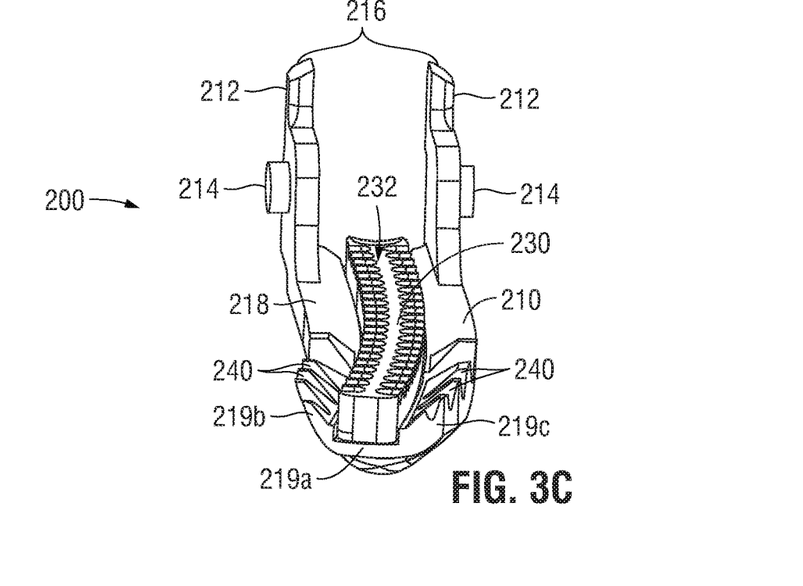

Referring to FIGS. 3A-3C, jaw member 200, includes a structural body 210 and a jaw liner 230. Structural body 210 includes a pair of proximal flanges 212 (each including a pivot boss 214 and a leg 216) and an elongated distal portion 218 extending distally from the pair of proximal flange 212. Structural body 210 is relatively rigid to provide integrity and support to jaw member 200 to enable jaw member 200 to apply sufficient clamping pressure to tissue grasped between jaw member and an opposing structure, e.g., blade 32 (FIGS. 1-2B). Structural body 210 may be fabricated from a metal, for example, stainless steel, or any other suitable material, and may be monolithically formed via machining, stamping, metal injection molding, or may be formed in any other suitable manner via any other suitable process.

Elongated distal portion 218 of structural body 210 of jaw member 200, as noted above, extends distally from the pair of proximal flanges 212. Elongated distal portion 218 may define a curved configuration, as illustrated, or may define a linear configuration or a different curved configuration. Elongated distal portion 218, more specifically, includes a base 219*a* and first and second sidewalls 219*b*, 219*c* disposed on either side of base 219*a*. Base 219*a* is configured to engage jaw liner 230, e.g., in complementary-fit engagement therewith.

Sidewalls 219*b*, 219*c* of elongated distal portion 218 of structural body 210 of jaw member 200 extend beyond a tissue-contacting surface 232 of jaw liner 230 on either side thereof, define gripping teeth 240, and extend along a distal portion of the length of elongated distal portion 218. More specifically, sidewalls 219*b*, 219*c* extend along a distal portion of elongated distal portion 218, for example, no more than a distal 50% of the length thereof, no more than a distal 40% of the length thereof, or no more than a distal 30% of the length thereof, in embodiments, although other configurations are also contemplated. The other portions of sidewalls 219*b*, 219*c* do not extend beyond tissue-contacting surface 232 of jaw liner 230, in embodiments. Gripping teeth 240 of sidewalls 219b, 219c may taper in height in the proximal-to-distal direction and/or may define decreased spacing therebetween in the proximal-to-distal direction, although other configurations are also contemplated.

By extending beyond tissue-contacting surface 232 of jaw liner 230, gripping teeth 240 facilitate maintaining tissue in position between jaw member 200 and an opposing structure, e.g., blade 32 (FIGS. 1-2B), during tissue treatment, thus inhibiting tissue slippage, all without interfering with the opposing structure, e.g., blade 32 (FIGS. 1-2B).

Figure 4A:
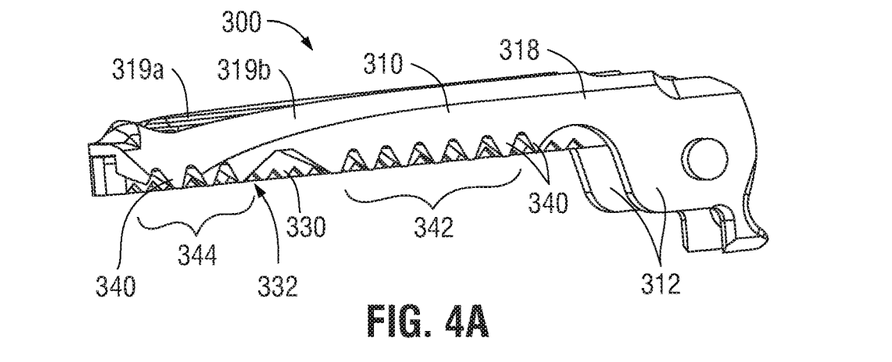
FIGS. 4A-4C are various views of another jaw member provided in accordance with the present disclosure and configured for use with the end effector of the ultrasonic surgical instrument of FIG. 1.
Figure 4B:
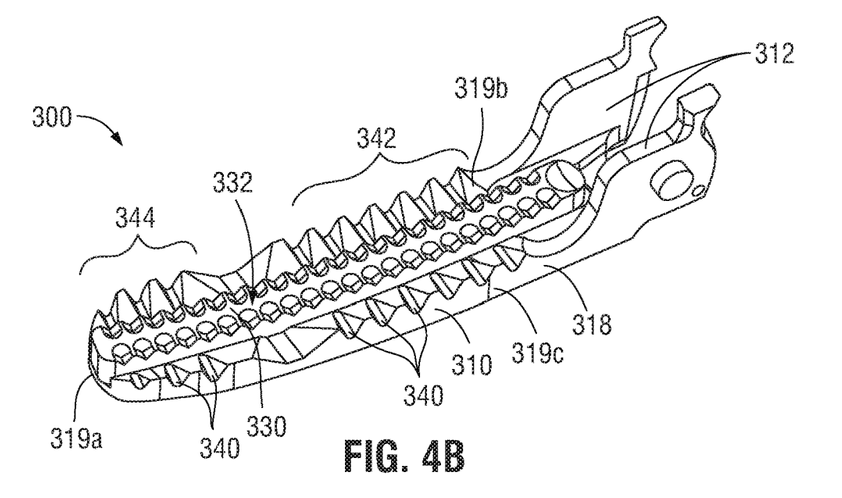
Figure 4C:
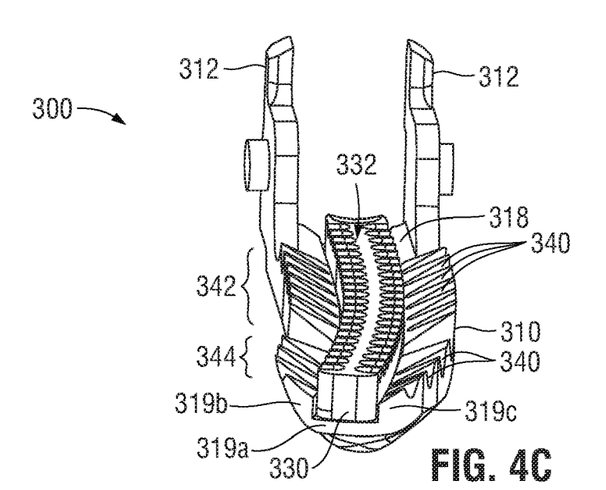

Referring to FIGS. 4A-4C, jaw member 300 is similar to jaw member 200 (FIGS. 3A-3C) and, thus, only differences therebetween are described in detail below. Jaw member 300 includes a structural body 310 and a jaw liner 330. Structural body 310 includes a pair of proximal flanges 312 and an elongated distal portion 318 extending distally from the pair of proximal flange 312.

Elongated distal portion 318 of structural body 310 of jaw member 300 includes a base 319a and first and second sidewalls 319b, 319c disposed on either side of base 319a. Base 319a is configured to engage jaw liner 330. Sidewalls 319b, 319c of elongated distal portion 318 of structural body 310 of jaw member 300 extend beyond a tissue-contacting surface 332 of jaw liner 330 on either side thereof, define gripping teeth 340, and extend along a substantial portion of the length of elongated distal portion 318, for example, at least 70% of the length thereof, at least 80% of the length thereof, or at least 90% of the length thereof, in embodiments, although other configurations are also contemplated. Gripping teeth 340 of sidewalls 319b, 319c may include a proximal portion of teeth 342, wherein the teeth 342 define substantially similar heights and spacing therebetween (within manufacturing tolerances), and a distal portion of teeth 344 that generally taper in height in the proximal-to-distal direction and/or may define decreased spacing therebetween in the proximal-to-distal direction, although other configurations are also contemplated.

Figure 5A:
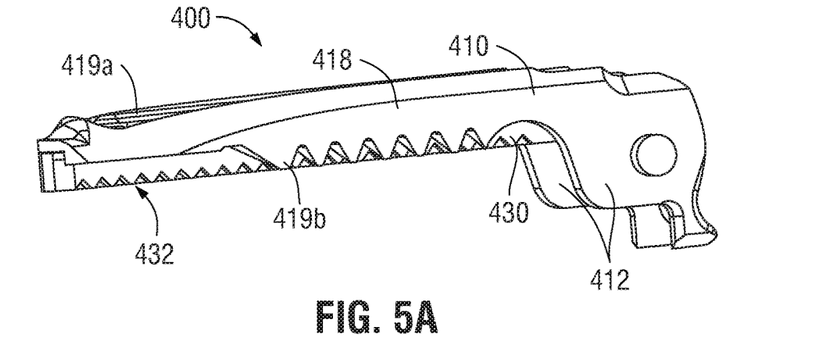
FIGS. 5A-5C are various views of yet another jaw member provided in accordance with the present disclosure and configured for use with the end effector of the ultrasonic surgical instrument of FIG. 1.
Figure 5B:
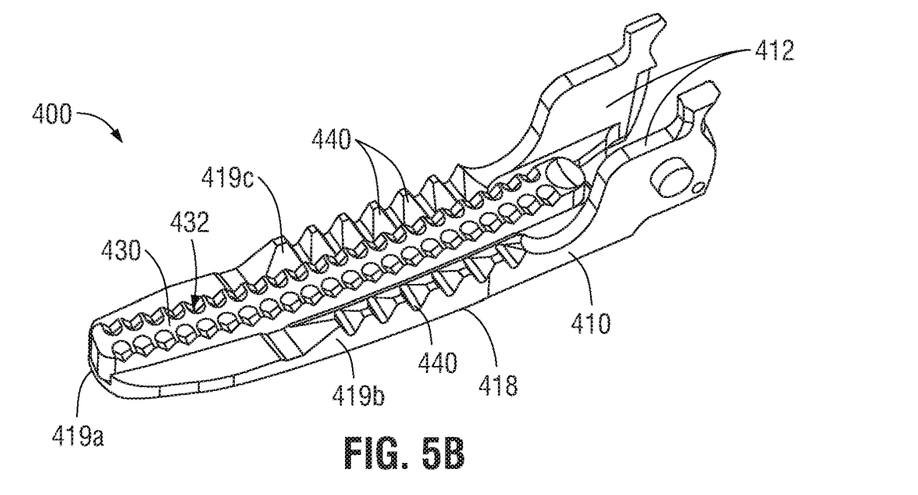
Figure 5C:
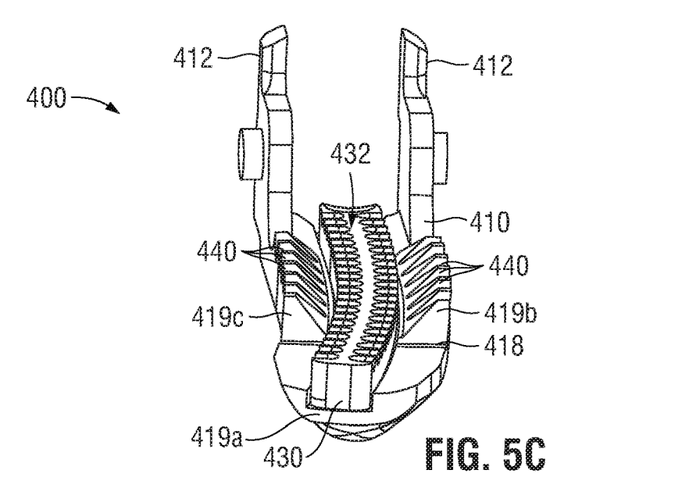

Referring to FIGS. 5A-5C, jaw member 400 is similar to jaw members 200, 300 (FIGS. 3A-3C and 4A-4C, respectively) and, thus, only differences therebetween are described in detail below. Jaw member 400 includes a structural body 410 and a jaw liner 430. Structural body 410 includes a pair of proximal flanges 412 and an elongated distal portion 418 extending distally from the pair of proximal flange 412.

Elongated distal portion 418 of structural body 410 of jaw member 400 includes a base 419a and first and second sidewalls 419b, 419c disposed on either side of base 419a. Base 419a is configured to engage jaw liner 430. Sidewalls 419b, 419c of elongated distal portion 418 of structural body 410 of jaw member 400 extend beyond a tissue-contacting surface 432 of jaw liner 430 on either side thereof, define gripping teeth 440, and extend along a proximal portion of the length of elongated distal portion 418, for example, no more than a proximal 750% of the length thereof, no more than a proximal 60% of the length thereof, or no more than a proximal 50% of the length thereof, in embodiments, although other configurations are also contemplated. Gripping teeth 440 of sidewalls 419b, 419c may define substantially similar heights and spacings therebetween (within manufacturing tolerances), although other configurations are also contemplated.

While several embodiments of the disclosure have been described above and illustrated in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A jaw member for a surgical instrument, the jaw member comprising:
   a rigid structural body including a proximal flange portion and an elongated distal portion extending distally from the proximal flange portion, the elongated distal portion defining a substantially flat proximal section, a distal section and a longitudinal axis and including a base and first and second sidewalls extending from either side of the base along at least a portion of a length of the elongated distal portion; and
   a compliant jaw liner engaged with the base of the elongated distal portion, the compliant jaw liner defining a tissue-contacting surface, the compliant jaw liner disposed between the first and second sidewalls such that first and second lateral edges of the compliant jaw liner are positioned adjacent and inwardly of the first and second sidewalls, respectively, wherein the tissue-contacting surface of the compliant jaw liner has a curved shape along the longitudinal axis,
   wherein the first and second sidewalls extend beyond the tissue-contacting surface of the compliant jaw liner, the first and second sidewalls configured to facilitate gripping tissue between the rigid structural body and an opposed structure,
   wherein the first and second sidewalls each define a plurality of gripping teeth along the distal section of the elongated distal portion, the gripping teeth having inner walls, the inner walls sloped toward the compliant jaw liner, the gripping teeth arranged along no more than 50% of the length of the elongated distal portion.

2. The jaw member according to claim 1, wherein the plurality of gripping teeth have substantially similar heights.

3. The jaw member according to claim 1, wherein at least two of the plurality of gripping teeth define different heights.

4. The jaw member according to claim 1, wherein the plurality of gripping teeth are substantially equally spaced along the sidewalls.

5. The jaw member according to claim 1, wherein at least two pairs of the plurality of gripping teeth are differently spaced along the sidewalls.

6. The jaw member according to claim 1, wherein the first and second sidewalls only extend along the distal section of the elongated distal portion of the rigid structural body.

7. The jaw member according to claim 1, wherein the first and second sidewalls extend along substantially the entire length of the elongated distal portion of the rigid structural body.

8. A surgical instrument, comprising:
   an energy-delivering component; and
   a jaw member positioned to oppose the energy-delivering component and movable relative thereto between an open position and a closed position for clamping tissue between the jaw member and the energy-delivering component, the jaw member including:
      a rigid structural body including a proximal flange portion and an elongated distal portion extending distally from the proximal flange portion, the elongated distal portion defining a substantially flat proximal section, a distal section and a longitudinal axis and including a base and first and second sidewalls extending from either side of the base along at least a portion of a length of the elongated distal portion; and a compliant jaw liner engaged with the base of the elongated distal portion, the compliant jaw liner defining a tissue-contacting surface, the compliant jaw liner disposed between the first and second sidewalls such that first and second lateral edges of the compliant jaw liner are positioned adjacent and inwardly of the first and second sidewalls, respectively, wherein the tissue-contacting surface of the compliant jaw liner has a curved shape along the longitudinal axis, wherein the first and second sidewalls extend beyond the tissue-contacting surface of the compliant jaw liner, the first and second sidewalls configured to facilitate gripping tissue between the rigid structural body and the energy-delivering component, wherein the first and second sidewalls each define a plurality of gripping teeth along the distal section of the elongated distal portion, the gripping teeth having inner walls, the inner walls sloped toward the compliant jaw liner, the gripping teeth arranged along no more than 50% of the length of the elongated distal portion.

9. The surgical instrument according to claim 8, wherein the energy-delivering component is an ultrasonic blade.

10. The surgical instrument according to claim 8, wherein the plurality of gripping teeth have substantially similar heights.

11. The surgical instrument according to claim 8, wherein at least two of the plurality of gripping teeth have different heights.

12. The surgical instrument according to claim 8, wherein the plurality of gripping teeth are substantially similarly spaced along the sidewalls.

13. The surgical instrument according to claim 8, wherein at least two pairs of the plurality of gripping teeth are differently spaced along the sidewalls.

14. The surgical instrument according to claim 8, wherein the first and second sidewalls only extend along the distal section of the elongated distal portion of the rigid structural body.

15. The surgical instrument according to claim 8, wherein the first and second sidewalls extend along substantially the entire length of the elongated distal portion of the rigid structural body.

16. An ultrasonic surgical instrument, comprising:

an ultrasonic blade configured to receive ultrasonic energy for treating tissue therewith, the ultrasonic blade defining a first width;

a jaw member movable relative to the ultrasonic blade between an open position and a closed position, the jaw member including:

a structural body including a proximal flange portion and an elongated distal portion extending distally from the proximal flange portion, the elongated distal portion defining a substantially flat proximal section, a distal section and a longitudinal axis and including a base and first and second sidewalls extending from either side of the base along at least a portion of a length of the elongated distal portion the first and second sidewalls spaced-apart a second width greater than the first width such that, in the closed position of the jaw member, the first and second sidewalls are disposed on either side of the ultrasonic blade; and a jaw liner engaged with the base of the elongated distal portion, the jaw liner defining a tissue-contacting surface, the jaw liner disposed between the first and second sidewalls such that first and second lateral edges of the jaw liner are positioned adjacent and inwardly of the first and second sidewalls, respectively, wherein the tissue-contacting surface of the jaw liner has a curved shape along the longitudinal axis, and wherein, in the closed position of the jaw member, the jaw and the ultrasonic blade are configured to clamp tissue therebetween, wherein the first and second sidewalls extend beyond the tissue-contacting surface of the jaw liner, the first and second sidewalls configured to facilitate gripping tissue, wherein the first and second sidewalls each define a plurality of gripping teeth along the distal section of the elongated distal portion, the gripping teeth having inner walls, the inner walls sloped toward the jaw liner, the plurality of gripping teeth arranged along no more than 50% of the length of the elongated distal portion.

* * * * *